United States Patent
Russo et al.

(10) Patent No.: US 6,573,411 B2
(45) Date of Patent: Jun. 3, 2003

(54) PROCESS FOR THE PREPARATION OF FLUOROPOLYOXYALKYLENES HAVING ONE END GROUP -CH2OH AND THE OTHER END GROUP CONTAINING CHLORINE

(75) Inventors: Antonio Russo, Milan (IT); Claudio Tonelli, Milan (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 10/146,044

(22) Filed: May 16, 2002

(65) Prior Publication Data

US 2002/0173679 A1 Nov. 21, 2002

(30) Foreign Application Priority Data

May 18, 2001 (IT) .......................... MI01A1034

(51) Int. Cl.$^7$ .................. C07C 43/11; C07C 43/18; C07C 41/00
(52) U.S. Cl. ............... 568/615; 568/618; 568/674; 568/675; 568/679; 568/689
(58) Field of Search ............... 568/615, 618, 568/674, 675, 679, 689

(56) References Cited

U.S. PATENT DOCUMENTS

| | | |
|---|---|---|
| 3,242,218 A | 3/1966 | Miller |
| 3,665,041 A | 5/1972 | Sianesi et al. .......... 260/615 A |
| 3,715,378 A | 2/1973 | Sianesi et al. |
| 3,766,251 A * | 10/1973 | Caporiccio et al. |
| 3,810,874 A | 5/1974 | Mitsch et al. |
| 4,523,039 A | 6/1985 | Lagow et al. ............. 568/615 |
| 5,144,092 A | 9/1992 | Marraccini et al. ......... 568/615 |
| 5,969,192 A * | 10/1999 | Marchionni et al. |
| 6,191,314 B1 * | 2/2001 | Wlassics et al. |

FOREIGN PATENT DOCUMENTS

| | | |
|---|---|---|
| EP | 0 148 482 A2 | 7/1985 |
| GB | 1104482 | 2/1968 |
| GB | 1309401 | 3/1973 |

* cited by examiner

*Primary Examiner*—Samuel Barts
*Assistant Examiner*—Sikarl A. Witherspoon
(74) *Attorney, Agent, or Firm*—Arent Fox Kintner Plotkin & Kahn PLLC

(57) ABSTRACT

A process to obtain fluoropolyoxyalkylenes having the structure:

$$T-O-(CF_2CF(CF_3)O)_{n-1}-(CF(CF_3)O)_m-CF_2-CH_2OH \quad (I)$$

wherein:
  T = $C_1$–$C_3$ perfluoroalkyl containing one Cl atom;
  n = an integer from 1 to 15; m/n = 0–0.5, m+n such to have a number molecular weight in the range 280–4,000;
said process comprising:
  a) the gradual addition of a metal hydride in admixture with a solvent to an ester precursor having the structure $$T-O-(CF_2CF(CF_3)O)_{n-1}-(CF(CF_3)O)_m-CF_2-COOR \quad (II)$$

wherein R = $C_1$–$C_{20}$ alkyl, or aromatic, cycloalkyl or heterocyclic residue,
  b) the hydrolysis of the reaction mixture obtained in step a) with an aqueous acid solution, the subsequent separation from the obtained organic phase of the compounds of structure (I).

7 Claims, No Drawings

PROCESS FOR THE PREPARATION OF FLUOROPOLYOXYALKYLENES HAVING ONE END GROUP -CH2OH AND THE OTHER END GROUP CONTAINING CHLORINE

The present invention relates to a process for the preparation of fluoropolyoxyalkylenes having at least one methylol end group —$CH_2OH$ and containing at least one chlorine atom in the other end group.

It is known in the prior art, for example GB 1,309,401 or U.S. Pat. No. 3,766,251, that the perfluoropolyethers with methylol end groups can be prepared by reduction of the corresponding perfluoropolyethers having —COOR end groups, wherein R is a $C_1$–$C_5$ alkyl group, in the presence of metal-hydrides reducing agents, such as lithium-aluminum hydride ($LiAlH_4$), sodium-boron hydride ($NaBH_4$), lithium-boron hydride ($LiBH_4$), in the presence of ethyl ether, dioxane, diglyme, tetrahydrofuran, or in the case of $NaBH_4$ in the presence of water or methanol, followed by the hydrolysis of the obtained reaction product by the aforesaid reduction.

The reduction reaction is carried out by directly adding a solution of perfluoropolyoxyalkylene alkylcarboxy ended in a solvent to a solution or suspension of the metal hydride in a solvent maintained under stirring at temperatures between 0°–100° C.

The reaction process scheme wherein a perfluoropolyether is used with an end group —$COOC_2H_5$ and $NaBH_4$ as reducing agent is as follows:

a) $2R_f$—$COOC_2H_5$+$NaBH_4$→($R_f$—$CH_2O)_2B(OC_2H_5)_2$ $Na^+$ b) ($R_f$—$CH_2O)_2B(OC_2H_5)_2^-Na^+$+$HCl$+$3H_2O$→$2R_f$— $CH_2OH$+$2C_2H_5OH$+$NaCl$+$H_3BO_3$ $R_f$=perfluoropolyoxyalkylene chain.

The Applicant has found that it is not possible to carry out said process, with high yields and selectivity, using as starting compounds fluoropolyethers having in their structure one end group cointaining at least one Cl atom and the other end group being a carboxylic ester, to obtain the corresponding fluoropolyethers with a methylol end group.

Besides, a hardly controllable self-catalytic decomposition of the reducing agent takes place, which implies significant process risks as regards its conduction bringing to very low and non reproducible yields in the desired product.

The need was therefore felt to prepare with high yields and selectivity, by a controllable process, fluoropolyethers having one end group containing one chlorine atom and the other end group being —$CH_2OH$.

The Applicant has unexpectedly found that it is possible to solve the above technical problem by starting from fluoropolyethers having one end group containing one Cl atom and the other end group a carboxylic ester to obtain with high yields and selectivity the corresponding fluoropolyethers with —$CH_2OH$ end groups.

It is therefore an object of the present invention a process to obtain fluoropolyoxyalkylenes having one end group containing one Cl atom and the other end group formed by a methylol group, having structure:

wherein:

T=$C_1$–$C_3$ perfluoroalkyl containing one Cl atom;
n=an integer from 1 to 15;
m/n=0–0.5;
m+n being such to have a number average molecular weight in the range 280–4,000, preferably 280–1,000, said process comprising the following steps:

a) the gradual addition, in inert gas atmosphere, of a mixture formed by an aprotic or protic solvent and a reducing agent selected from the metal hydrides class, to an ester precursor having the structure

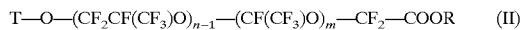

wherein T, m, n have the above meaning and R represents a $C_1$–$C_{20}$ alkyl, aromatic, cycloalkyl or heterocyclic residue, said residues being optionally substituted, maintaining the reaction mixture under stirring at a temperature in the range 0°–20° C., preferably 5° C.–15° C.;

b) hydrolysis of the reaction product obtained in step a) with an aqueous acid solution, with formation of an aqueous phase and of an organic phase, and the subsequent separation from the organic phase of the compounds of structure (I) having one end group —$CH_2OH$ and the other one containing Cl.

The ester precursor (II) can optionally be used in admixture with an aprotic or protic solvent.

The solvents for the reducing agent and for the ester precursor can be aprotic solvents, such as for example tetrahydrofuran, diglyme, dioxane or protic solvents as for example methanol, ethanol, isopropanol, isobutanol, preferably ethanol. It is possible to use mixtures of the aforesaid solvents.

As reducing agents, metal hydrides can be used, such as for example lithium-aluminum hydride ($LiAlH_4$), sodium-boron hydride ($NaBH_4$), lithium-boron hydride ($LiBH_4$) dissolved or in suspension in the above solvents. Preferably a solution or a suspension containing 0.1–15% by weight of sodium-boron hydride ($NaBH_4$) is used. The $NaBH_4$ amount with respect to the ester precursor (II) is comprised between the stoichiometric reaction value and an excess of 30%.

Step b) of hydrolysis and separation of the compound (I) is carried out by known methods. Generally the hydrolysis is carried out by gradually adding the reaction compound obtained in step a) to an aqueous solution of HCl, preferably at a concentration of 5–10% by weight, in an amount at least equiponderal with respect to the precursor (II). The addition of the compounds obtained from step a) to the acid solution is gradually carried out as the optional excess of the unreacted reducing agent hydrolyzes developing gaseous hydrogen. At the end of step b), several aqueous washings can optionally be carried out to completely remove the inorganic salts from the reduced fluorinated compound (I).

The hydrolysis of the reaction mixture of step a) can also be carried out by directly adding to said mixture the aqueous acid solution.

By the process of the present invention it is possible to obtain a complete conversion of the starting ester, a selectivity higher than 99% and an yield on the separated compound higher than or equal to 90%, preferably higher than or equal to 95%.

Furthermore in the present process hydrogen develops only in limited amounts with remarkable advantages as regards the conduction and safety of the process in an industrial plant.

Step a) of the process reduction of the present invention can be carried out in the presence of stabilizers of the reducing agent such the alkaline metal alcoholates, for example sodium ethylate.

The present process, characterized in that the reduction reaction is carried out by gradually adding a solution or suspension of the reducing agent to the fluoroether (II) to be reduced, can be used to reduce fluoroalkanes or fluoroethers free from end groups containing Cl but containing at least one —COOR end group with R as above defined.

In other words by using fluorinated esters as precursors it is possible to obtain the corresponding fluoroethers or fluoroalkanes having at least one methylol —CH$_2$OH group with high conversions and selectivity higher than 99% by using a limited excess of the reducing agent, generally lower than 30% of the stoichiometric value.

As precursors to be reduced, monofunctional or bifunctional perfluoropolyethers having the following general formula:

$$T_1—CFW_1—O—R_{f1}—CFW_2—T_2 \quad (III)$$

can be used, wherein:
  $T_1$, $T_2$, equal to or different from each other, are selected from end groups of the —COOR type, or —F, —CF$_3$, —CF$_2$CF$_3$ with the proviso that at least one between $T_1$ and $T_2$ is —COOR;
  $W_1$ and $W_2$, equal to or different from each other, are F, CF$_3$; $R_{f1}$ is a perfluoropolyoxyalkylene chain having a number average molecular weight in the range 300–10,000 comprising one or more repeating units of —CF$_2$CF$_2$O—, —(CF$_2$CF(CF$_3$)O)—, —(CF(CF$_3$)CF$_2$O)— —CF$_2$(CF$_2$)$_z$CF$_2$O—, —CR$_4$R$_5$CF$_2$CF$_2$O— type;
wherein:
  z is an integer equal to 1 or 2;
  Y is F or CF$_3$;
  $R_4$ and $R_5$, equal to or different from each other, are selected from H, linear or branched perfluoroalkyl having a number of C atoms from 1 to 4;
  said units being statistically distributed along the perfluoropolyoxyalkylene chain.

In particular the following $R_{f1}$ perfluoropolyethers can be mentioned as preferred:

(A) —(CF$_2$CF(CF$_3$)O)$_a$(CFYO)$_b$—
  wherein Y is F or CF$_3$; a and b are integers such that the molecular weight is comprised in the above range; a/b is comprised between 10 and 100;
  or the repeating units shown in (A) can be linked as follows:
  —(CF$_2$CF(CF$_3$)O)$_a$(CFYO)$_b$—CF$_2$(R'$_f$)CF$_2$—O—(CF$_2$CF(CF$_3$)O)$_a$(CFYO)$_b$— wherein R'$_f$ is a fluoroalkylene group from 1 to 4 C. atoms;

(B) —(CF$_2$CF$_2$O)$_c$(CF$_2$O)$_d$(CF$_2$(CF$_2$)$_z$O)$_h$—
  wherein c, d and h are integers such that the molecular weight is comprised in the above range; c/d is comprised between 0.1 and 10; h/(c+d) is comprised between 0 and 0.05, z has the above value, h can also be equal to 0;

(C) —(CF$_2$CF(CF$_3$)O)$_e$(CF$_2$CF$_2$O)$_f$(CFYO)$_g$—
  wherein Y is F or CF$_3$; e, f, g are integers such that the molecular weight is comprised in the above range; e/(f+g) is comprised between 0.1 and 10, f/g is comprised between 2 and 10;

(D) —(CF$_2$(CF$_2$)$_z$O)$_s$—
  wherein s is an integer such as to give the above molecular weight, z has the already defined meaning;

(E) —(CR$_4$R$_5$CF$_2$CF$_2$O)$_{j'}$—
  wherein $R_4$ and $R_5$ are equal to or different from each other and selected between H or perfluoroalkyl, for example having 1–4 C atoms, j' being an integer such that the molecular weight is the above mentioned one; said units inside the fluoropolyoxyalkylene chain can be linked each other as follows:
  —(CR$_4$R$_5$CF$_2$CF$_2$O)$_{p'}$—R'$_f$—O—(CR$_4$R$_5$CF$_2$CF$_2$O)$_{q'}$—
    wherein R'$_f$ is a fluoroalkylene group, for example from 1 to 4 C atoms, p' and q' are integers such that the molecular weight is the above mentioned one;

(F) —(CF(CF$_3$)CF$_2$O)$_{j''}$—
  j'' being an integer such as to give the above molecular weight.

(A) and (B) are the particularly preferred structures.

These structures comprising the mentioned repeating units and the methods for preparing them are described in the patents GB 1,104,482, U.S. Pat. No. 3,242,218, U.S. Pat. No. 3,665,041, U.S. Pat. No. 3,715,378, EP 148,482, U.S. Pat. No. 4,523,039, U.S. Pat. No. 5,144,092, and for their functional derivatives see for example U.S. Pat. No. 3,810,874. All these patents are incorporated herein by reference.

Compared to the processes of the prior art wherein the reduction is carried out, by adding the perfluoropolyether ester to a solution containing the reducing agent, the present process requires a lower amount of the reducing agent and it can be industrially carried out with the significant advantage that during the process lower amounts of hydrogen develop. More specifically the Applicant has found that by gradually adding the reducing agent, in solution or in suspension in a solvent, to a fluoropolyoxyalkylene carboxyended with the other end group containing one Cl atom, maintaining the reaction mixture at a temperature in the range 0° C.–20° C., it is possible to obtain the corresponding fluoropolyoxyalkylenes having methylol end groups —CH$_2$OH, with quantitative conversions and yields at least equal to 90, preferably at least equal to 95%, using a limited excess of the reducing agent with respect to the stoichiometric value, and with the reduction to values lower than 1% molar in undesired by-products having one end group containing one H atom derived from the transformation of the end group containing one Cl atom.

The present invention will be better illustrated by the following Examples, which have a merely indicative but not limitative purpose of the scope of the invention itself.

EXAMPLES

Example 1

A 3 liters reactor equipped with cooling jacket, mechanical stirrer and directly connected to a volumetric gas reader, is charged with 200 g (0.32 moles) of a fluoropolyoxyalkylene ester of general formula A—(CF(CF$_3$)CF$_2$O)$_{n-1}$—CF$_2$—COOC$_2$H$_5$ wherein A is the CF$_3$—CFCl—CF$_2$—O— group for 60% and the CF$_2$Cl—CF(CF$_3$)—O— group for 40%, having n comprised between 2 and 5 selected so that the average molecular weight MW=617. The ester temperature is then brought to 5° C., maintaining the temperature of the external jacket at 0° C. 226 g of a solution of 8 g of NaBH$_4$ (0.2 moles) in 218 g of ethanol are fed under stirring. By maintaining constant the temperature in the jacket (0° C.)

for the whole feeding period (35 minutes), the temperature inside the reactor rises up to 10° C. During the reaction 2.6 liters of $H_2$ are developed. At the end of the feeding the intermediate boric esters are hydrolyzed, by adding 400 g of an aqueous HCl solution at 10% by weight, and contemporaneously the unreacted sodium-boron hydride is titred, volumetrically measuring the developed $H_2$ moles. The developed hydrogen volume resulted equal to 1.7 liters (0.07 moles), equivalent to 0.7 g (0.019 moles) of $NaBH_4$. During the reaction an excess of $NaBH_4$ equal to 12% with respect to the stoichiometric value was therefore consumed.

After the addition of the HCl solution, the reaction mixture is let under stirring at room temperature for about one hour. The phases are allowed to separate and the organic phase is stripped at 60° C./1 mmHg. 182 g of compound are obtained which is analyzed by IR and NMR. The yield results equal to 97%.

The analyses are in accordance with the total reduction of the ester to the alcohol of formula $Cl(C_3F_6O)_n$—$CF_2$—$CH_2OH$ (MW=588) and, besides, the final compound contains only 0.6% by moles of hydrogenated compounds of formula $H(C_3F_6O)_n$—$CF_2$—$CH_2OH$.

Example 2

By using the equipment reported in Example 1, 200 g (0.2 moles) of a fluoropolyoxyalkylene ester of general formula A—$(C_3F_6O)_4$—$CF_2$—$COOC_2H_5$ wherein A is the $CF_3$—CFCl—$CF_2$—O— group for 60% and the $CF_2Cl$—CF($CF_3$)—O— group for 40%, having an average molecular weight MW=988, are charged in the reactor. 141 g of a solution of 5 g of $NaBH_4$ (0.13 moles) in 136 g of ethanol are fed under stirring. By maintaining constant the temperature in the jacket (0° C.) for the whole feeding period (25 minutes), the temperature inside the reactor rises up to 12° C. During the reaction 1.5 liters of $H_2$ are developed. At the end of the feeding the intermediate boric esters are hydrolyzed, by adding 400 g of an aqueous HCl solution at 10% by weight, and contemporaneously the unreacted sodium-boron hydride is titred, volumetrically measuring the developed $H_2$ moles. The developed hydrogen volume resulted equal to 1.4 liters (0.06 moles), equivalent to 0.57 g (0.015 moles) of $NaBH_4$. During the reaction an excess of $NaBH_4$ equal to 15.8% with respect to the stoichiometric value was therefore consumed.

After the addition of the HCl solution, the reaction mixture is let under stirring at room temperature for about one hour. Then the phases are allowed to separate and the organic phase is stripped at 60° C./1 mmHg. 186 g of compound are obtained which is analyzed by IR and NMR. The yield results equal to 98%.

The analyses are in accordance with the total reduction of the ester to the alcohol of formula $Cl(C_3F_6O)_5$—$CF_2$—$CH_2OH$ (MW=946), besides, the final compound contains only 0.4% by moles of hydrogenated compounds of formula $H(C_3F_6O)_5$—$CF_2$—$CH_2OH$.

Example 3

Comparative

By using the equipment reported in Example 1, 218 g of ethanol and 8 g of $NaBH_4$ (0.20 moles) are charged in the reactor. The reaction mixture is then brought to 5° C., maintaining the temperature of the external jacket at 0° C. Under stirring one starts to feed, with a flow-rate of 150 g/h, 200 g (0.32 moles) of a fluoropolyoxyalkylene ester of general formula A—$(C_3F_6O)_{n-1}$—$CF_2$—$COOC_2H_5$ wherein A is the $CF_3$—CFCl—$CF_2$—O— group for 60% and the $CF_2Cl$—CF($CF_3$)—O— group for 40%, having n comprised between 2 and 5 such that the average molecular weight MW=617. When 50.8 g of the ester have been fed, feeding must be stopped owing to a sudden increase of the temperature which passes from 9° C. to 35° C. in about 1 minute, with development of about 7 liters of hydrogen, which, together with 1.8 liters of $H_2$, developed until that moment, amounts in the whole to 8.8 liters.

The intermediate boric esters are hydrolyzed, by adding 400 g of an aqueous HCl solution at 10% by weight. During the hydrolysis, development of hydrogen is not noticed, therefore during the reaction a total decomposition of the sodium-boron hydride present in the reactor occurred.

After the addition of the HCl solution, the reaction mixture is let under stirring at room temperature for about one hour. Then the phases are allowed to separate and the organic phase is stripped at 60° C./1 mmHg and then analyzed by IR and NMR.

The analyses on the obtained compound show the presence of 65% by moles of hydrogenated compounds of formula $H(C_3F_6O)_{n-CF2}$—$CH_2OH$ against only 35% of $Cl(C_3F_6O)_n$—$CF_2$—$CH_2OH$.

What is claimed is:

1. A process to obtain fluoropolyoxyalkylenes having one end group containing one Cl atom and the other end group containing a methylol group, having structure:

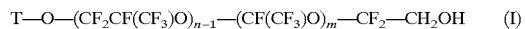

T—O—$(CF_2CF(CF_3)O)_{n-1}$—$(CF(CF_3)O)_m$—$CF_2$—$CH_2OH$   (I)

wherein:

T=$C_1$–$C_3$ perfluoroalkyl containing one Cl atom;

n=an integer from 1 to 15;

m/n=0–0.5;

m+n being such to have a number average molecular weight in the range 280–4,000, said process comprising the following steps:
a) the gradual addition, in inert gas atmosphere, of a mixture formed by an aprotic or protic solvent and a reducing agent selected from the metal hydrides class, to an ester precursor having the structure

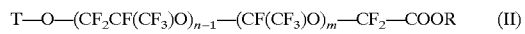

T—O—$(CF_2CF(CF_3)O)_{n-1}$—$(CF(CF_3)O)_m$—$CF_2$—COOR   (II)

wherein

T, m, n have the above meaning;

R represents a $C_1$–$C_{20}$ alkyl, aromatic, cycloalkyl or heterocyclic residue, said residues being optionally substituted, maintaining the reaction mixture under stirring at a temperature in the range 0°–20° C.;
b) hydrolysis of the reaction product obtained in step a) with an aqueous acid solution, with formation of an aqueous phase and of an organic one, and the sub sequent separation from the organic phase of the compounds of structure (I) having one end group —$CH_2OH$ and the other one containing one chlorine atom.

2. A process according to claim 1, wherein the ester precursor (II) is used in admixture with an aprotic or protic solvent.

3. A process according to claim 2, wherein the aprotic solvents are selected from the group formed by tetrahydrofuran, diglyme, dioxane and the protic solvents are selected from the group formed by methanol, ethanol, isopropanol, isobutanol or mixtures thereof.

4. A process according to claim 1, wherein the reducing agent is selected from the group formed by lithium-aluminum hydride ($LiAlH_4$), sodium-boron hydride ($NaBH_4$), lithium-boron hydride ($LiBH_4$).

5. A process according to claim 4, wherein the reducing agent is sodium-boron hydride ($NaBH_4$), used in an amount with respect to the ester precursor (II) comprised between the reaction stoichiometric value and an excess of 30%.

6. A process according to claim 1, wherein the hydrolysis step b) is carried out either by gradually adding the reaction mixture obtained in step a) to a HCl solution at 5–10% by weight, or by gradually adding said HCl solution to the reaction mixture obtained in step a).

7. A process according to claim 1, wherein the reducing agent is used in admixture with alkaline metals alcoholates as stabilizers.

* * * * *